United States Patent
Zhang et al.

(10) Patent No.: US 11,260,166 B2
(45) Date of Patent: Mar. 1, 2022

(54) ANTI-REFLUX TUBE-TYPE ENEMATOR

(71) Applicant: Ningbo Albert Novosino Co., Ltd, Ningbo (CN)

(72) Inventors: Yonggui Zhang, Ningbo (CN); Haibo Hu, Ningbo (CN)

(73) Assignee: NINGBO ALBERT NOVOSINO CO., LTD, Ningbo (CN)

( * ) Notice: Subject to any disclaimer, the term of this patent is extended or adjusted under 35 U.S.C. 154(b) by 264 days.

(21) Appl. No.: 16/585,339

(22) Filed: Sep. 27, 2019

(65) Prior Publication Data

US 2020/0390962 A1 Dec. 17, 2020

(30) Foreign Application Priority Data

Jun. 13, 2019 (CN) .......................... 201910512359.X
Jun. 13, 2019 (CN) .......................... 201920888857.X
Jul. 12, 2019 (CN) .......................... 201930371664.X

(51) Int. Cl.
*A61M 3/02* (2006.01)

(52) U.S. Cl.
CPC ........ *A61M 3/0262* (2013.01); *A61M 3/0216* (2014.02); *A61M 3/0279* (2013.01)

(58) Field of Classification Search
CPC .............. A61M 3/0262; A61M 3/0216; A61M 3/0279; A61M 3/0208; A61M 2039/2493; A61M 39/24; A61M 15/0013; A61M 15/0018
See application file for complete search history.

(56) References Cited

U.S. PATENT DOCUMENTS

| 703,615 | A | * | 7/1902 | Schwartz | ............ | A61M 3/0279 |
| | | | | | | 604/278 |
| 5,261,459 | A | * | 11/1993 | Atkinson | ............... | A61M 39/24 |
| | | | | | | 137/846 |
| 2010/0308133 | A1 | * | 12/2010 | Yeh | ...................... | A61M 3/0262 |
| | | | | | | 239/327 |
| 2017/0281881 | A1 | * | 10/2017 | Trevino | ................... | A61M 1/82 |
| 2020/0215257 | A1 | * | 7/2020 | Hagen | ................. | A61M 3/0262 |

* cited by examiner

*Primary Examiner* — Theodore J Stigell
*Assistant Examiner* — Rachel T. Smith
(74) *Attorney, Agent, or Firm* — Thomas | Horstemeyer, LLP

(57) ABSTRACT

Disclosed are various embodiments for an anti-reflux tube-type enemator that is leakproof, easy-to-clean, and quickly inflates to provide a steady flow of solution. The anti-reflux enemator includes a nozzle comprising a nozzle outlet, a tube fluidly coupled to the nozzle, and an enema bulb fluidly coupled to the tube. The enema bulb is configured to store solution therein and, in response to a squeezing force applied to the enema bulb, direct the solution through the tube and the nozzle, and expel the solution through the nozzle outlet. An anti-reflux coupler is positioned between the enema bulb and the tube through which the solution passes from the enema bulb to the tube. One or more one-way air valves are positioned relative to an aperture of the enema bulb.

19 Claims, 9 Drawing Sheets

ANTI-REFLUX TUBE-TYPE ENEMATOR

CROSS-REFERENCE TO RELATED APPLICATIONS

This application claims the benefit of and priority to Chinese Patent Application No. 201930371664.2 filed Jul. 12, 2019, Chinese Patent Application No. 201920888857.X filed Jun. 13, 2019, and Chinese Patent Application No. 201910512359.X filed Jun. 13, 2019, the contents of which being incorporated by reference in their entireties herein.

TECHNICAL FIELD

This invention belongs to the technical field of enemators and, more specifically, describes an anti-reflux, leakproof, easy-to-discharge, easy-to-clean, and easy-to-seal tube-type enemator.

BACKGROUND

Enemators include syringe-type devices that can be utilized by patients and medical practitioners for cleansing the body, such as vaginal, anal, and other bodily cavities. Generally, enemators are filled with solution, such as clean or soapy water, which is injected into a cavity of a person by hand squeezing a bulb or similar apparatus. During this process, the solution may "reflux," where some solution is returned into the enemator, thereby contaminating the solution and affecting the use of conventional enemators.

Moreover, many types of enemators do not prevent leakage of solution. For instance, due to poor design and manufacturing, existing enemators in the art are unable to store solution for a long period of time without leakage. To address this, some enemators use a fixed leakproof structure so that they are not easy to clean, have a limited length of use, and a high purchasing cost. Also, a joint line on the side of the connected syringe nozzle exists in some enemators to ease manufacturing costs; however, the joint line often scratches the human body or is otherwise uncomfortable during use. Due to poor manufacturing and design, the outlet of the syringe nozzle is easily blocked, leading to a poor user experience.

BRIEF SUMMARY OF INVENTION

Disclosed are various embodiments for an anti-reflux tube-type enemator that is leakproof, easy-to-clean, easy to disassemble and reassemble, has part swapability, and quickly inflates to provide a steady flow of solution when cleaning a bodily cavity. An anti-reflux enemator includes a nozzle comprising a nozzle outlet, a tube fluidly coupled to the nozzle, and an enema bulb fluidly coupled to the tube. The enema bulb is configured to store solution therein and, in response to a squeezing force applied to the enema bulb, direct the solution through the tube and the nozzle and expel the solution through the nozzle outlet. An anti-reflux coupler is positioned between the enema bulb and the tube through which the solution passes from the enema bulb to the tube. One or more one-way air valves are positioned relative to an aperture of the enema bulb.

In some embodiments, the anti-reflux enemator includes a first threaded connection for detachably attaching the anti-reflux coupler to the enema bulb, a second threaded connection for detachably attaching the tube to the anti-reflux coupler, and a third threaded connection for detachably attaching the nozzle to the tube. As such, the anti-reflux enemator can be described as have four principal components, each of which being removable from one another, such as the nozzle, the tube, the anti-reflux coupler, and the enema bulb.

In further embodiments, the anti-reflux enemator includes a first sealing ring configured to prevent leakage occurring at the first threaded connection, a second sealing ring configured to prevent leakage occurring at the second threaded connection, and a third sealing ring configured to prevent leakage occurring at the third threaded connection. The at least one one-way air valve can include a first one-way air valve and a second one-way air valve positioned relative to the aperture located at a base of the enema bulb.

In some embodiments, the nozzle of the anti-reflux enemator is a first nozzle having a first predetermined size and shape. The anti-reflux enemator can further include a second nozzle having a second predetermined size and shape different from the first predetermined size and shape, where the second nozzle is configured to replace the first nozzle via the third threaded connection.

The anti-reflux coupler can further include a check valve, the check valve comprising the anti-reverse diaphragm. For instance, the check valve can include one of: an umbrella valve; a duckbill valve; a slit-cutting valve; and a flapper valve. In some embodiments, the check valve is a silicone check valve comprising a step seal surface.

The nozzle can include an inclined nozzle surface such that a bottom portion of the nozzle has a width less than a top portion of the nozzle. Additionally, in some embodiments, the nozzle can include a calabash-shaped syringe pipe body.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Figure 1:
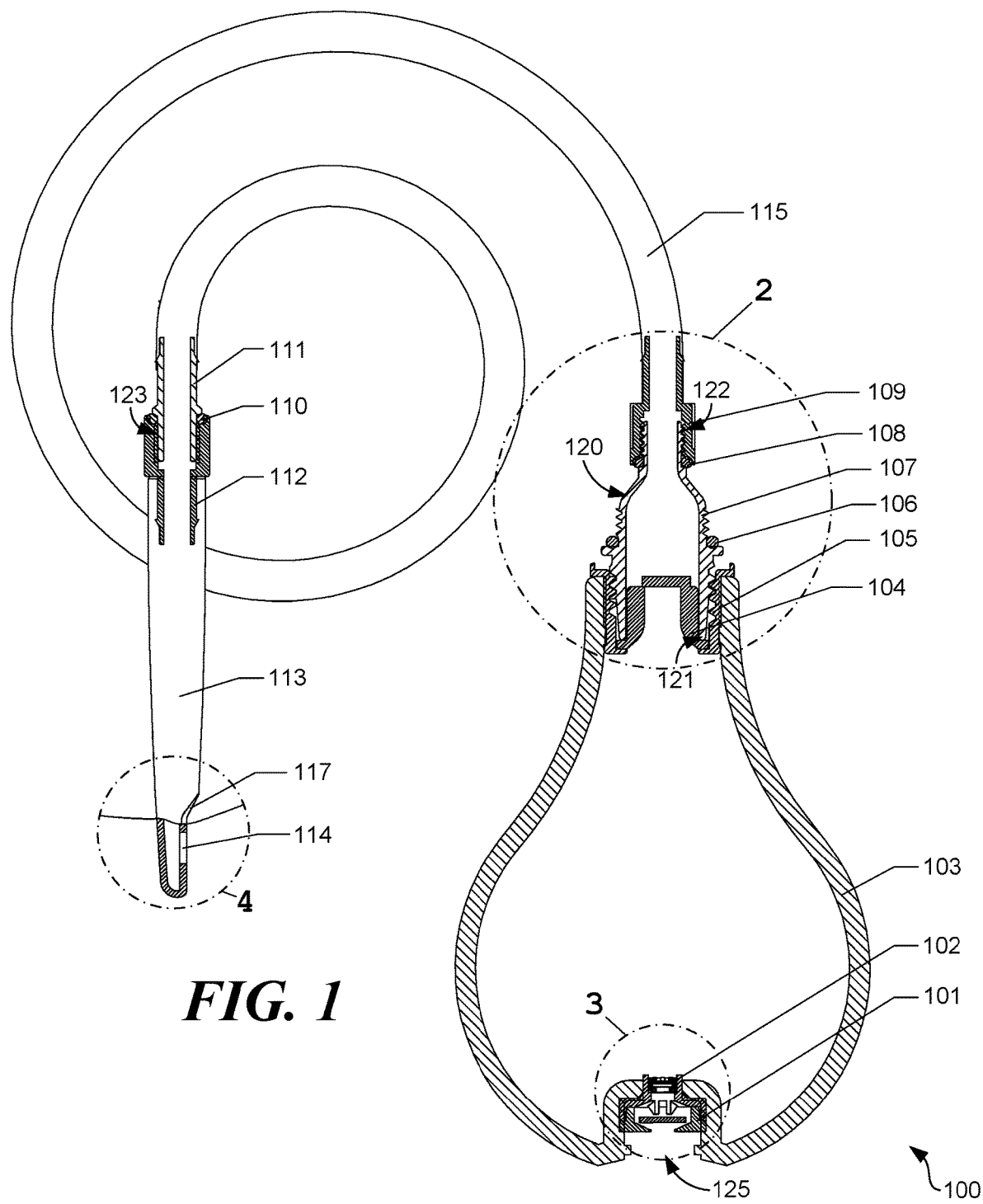
FIG. 1 is a cross-sectional view of an anti-reflux tube-type enemator according to various embodiments of the present disclosure.
Figure 2:
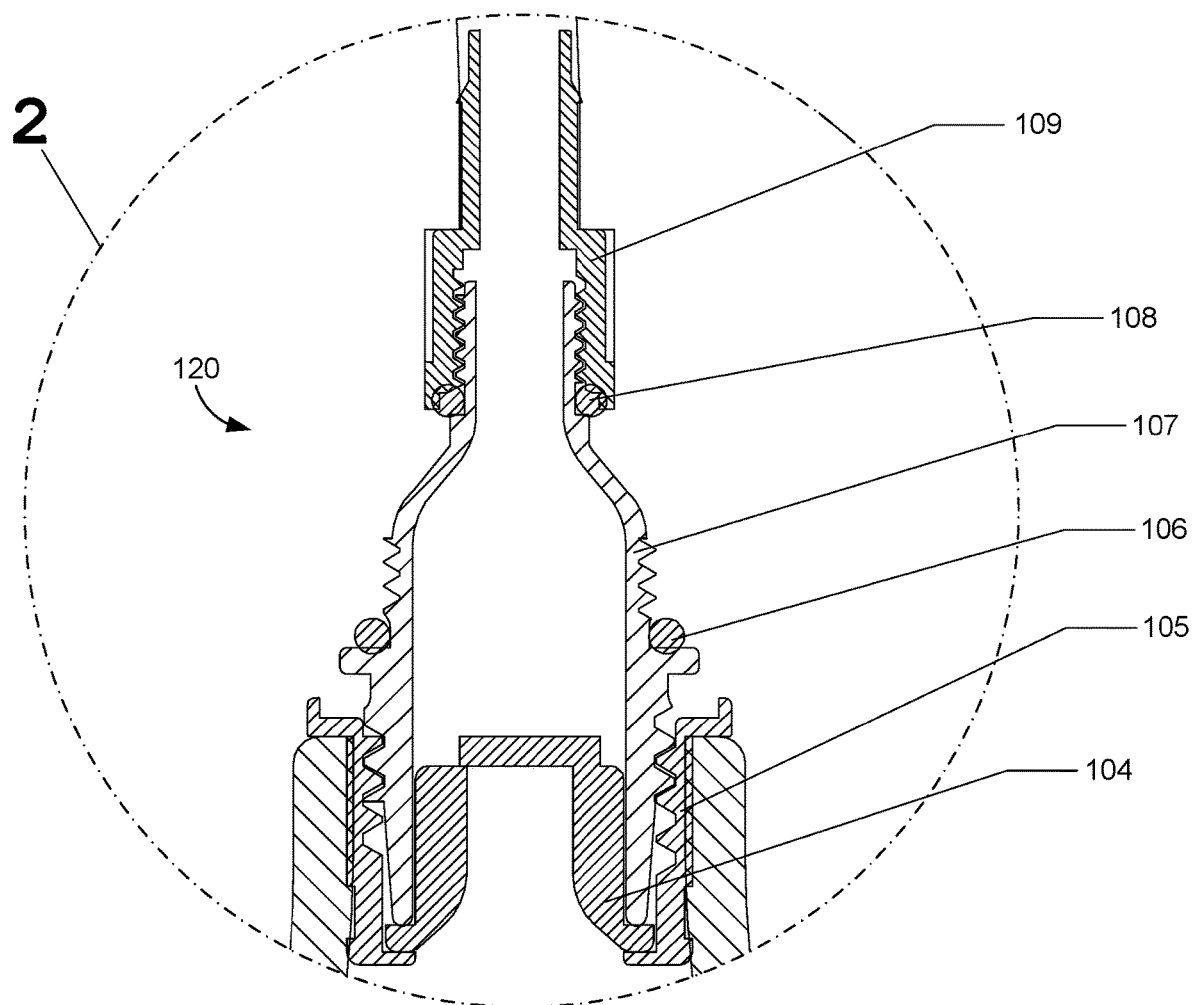
FIG. 2 is a partial enlarged view of callout region 2 of FIG. 1 according to various embodiments of the present disclosure.

The present disclosure generally relates to an anti-reflux enemator having a tube portion that is leak resistant and easy to assemble and clean. Some existing enemators include a tube portion that provides an operator with flexibility with respect to placement of a nozzle. However, existing enemators include enemator bulbs capable of being pressed a single time when used, requiring the operator to wait a notable period of time for the bulb to expand to again squeeze the bulb. Moreover, it is difficult to clean tubes of existing enemators as it can be difficult or impossible to disassemble existing devices as many enemators are integrally formed to provide low manufacturing costs. As bulbs on existing enemators can't be continuously pressed, the bulb may bounce back very slowly, increasing the time needed to perform a cleaning operation. Finally, existing enemators do not include a simple structure and function, are costly to manufacture, and are inconvenient to operate.

Accordingly, various embodiments are described for an anti-reflux enemator with a tube, where the anti-reflux enemator includes an enemator bulb capable of continuously being pressed to provide a continuous and constant stream of water when performing an enema or similar cleaning procedure. The anti-reflux enemator includes one or more syringe pipes having different lengths, diameters, shapes, and sizes which permits the operator to select a most suitable syringe pipe for a given application.

The enemator bulb described herein can be continuously pressed and, as such, can bounce back quickly by virtue of a one-way outlet air valve positioned, for instance, at a bottom of the enemator bulb. The anti-reflux enemator with a tube described herein provides little or no leakage despite the presence of the valve. An improved transparent tip and dipping tip is provided without a flash or welding line, that can be uncomfortable for users. Finally, the anti-reflux enemator is configured to be easily disassembled, which facilitates cleaning or quick changing of various components. Additional benefits may become apparent after a full viewing of the present disclosure.

According to various embodiments, an anti-reflux enemator includes a nozzle comprising a nozzle outlet, a tube fluidly coupled to the nozzle, and an enema bulb fluidly coupled to the tube. The enema bulb is configured to store solution therein and, in response to a squeezing force applied to the enema bulb, direct the solution through the tube and the nozzle, and expel the solution through the nozzle outlet. An anti-reflux coupler is positioned between the enema bulb and the tube through which the solution passes from the enema bulb to the tube. One or more one-way air valves are positioned relative to an aperture of the enema bulb.

In some embodiments, the anti-reflux enemator includes a first threaded connection for detachably attaching the anti-reflux coupler to the enema bulb, a second threaded connection for detachably attaching the tube to the anti-reflux coupler, and a third threaded connection for detachably attaching the nozzle to the tube. As such, the anti-reflux enemator can be described as have four principal components, each of which being removable from one another, such as the nozzle, the tube, the anti-reflux coupler, and the enema bulb.

In further embodiments, the anti-reflux enemator includes a first sealing ring configured to prevent leakage occurring at the first threaded connection, a second sealing ring configured to prevent leakage occurring at the second threaded connection, and a third sealing ring configured to prevent leakage occurring at the third threaded connection. The at least one one-way air valve can include a first one-way air valve and a second one-way air valve positioned relative to the aperture located at a base of the enema bulb.

In some embodiments, the nozzle of the anti-reflux enemator is a first nozzle having a first predetermined size and shape. The anti-reflux enemator can further include a second nozzle having a second predetermined size and shape different from the first predetermined size and shape, where the second nozzle is configured to replace the first nozzle via the third threaded connection.

The anti-reflux coupler can further include a check valve, the check valve comprising the anti-reverse diaphragm. For instance, the check valve can include one of: an umbrella valve; a duckbill valve; a slit-cutting valve; and a flapper valve. In some embodiments, the check valve is a silicone check valve comprising a step seal surface.

The nozzle can include an inclined nozzle surface such that a bottom portion of the nozzle has a width less than a top portion of the nozzle. Additionally, in some embodiments, the nozzle can include a calabash-shaped syringe pipe body.

Referring now to FIGS. 1 to 10, various views and embodiments for an anti-reflux enemator 100 are shown. Specifically, FIG. 1 includes a cross-section view of the anti-reflux enemator 100. FIG. 1 includes callout region 2, callout region 3, and callout region 4 of the cross-section view of FIG. 1 that are reproduced in an enlarged manner in FIGS. 2, 3, and 4, respectively.

Referring collectively to FIGS. 1 to 10, in some embodiments, the anti-reflux enemator 100 includes a first one-way air valve 101 (e.g., a first check valve), a second one-way air valve 102 (e.g., a second check valve), an enema bulb 103, a check valve 104 (e.g., a third check valve), a first internal thread connector 105, a first sealing ring 106, a first external thread connector 107, a second seal ring 108, a second internal thread connector 109, a third sealing ring 110, a second external thread connector 111, a third internal thread connector 112, a nozzle 113, an outlet 114 (e.g., a "nozzle outlet"), a tube 115, an inclined nozzle surface 117, a sealing step surface 118, a second nozzle 119 (e.g., a calabash-shaped syringe pipe), as well as other components as will be described.

Generally, the anti-reflux enemator 100 can include four principal components that are detachably attachable to one another, such as the nozzle 113, the tube 115, the enema bulb 103, and an anti-reflux coupler 120. As shown in the enlarged view of callout region 2 in FIGS. 1 and 2, the anti-reflux coupler 120 includes the check valve 104, the first internal thread connector 105, the first sealing ring 106, the first external thread connector 107, the second seal ring 108, the second internal thread connector 109, as well as other components.

The anti-reflux enemator 100 can include a nozzle 113 comprising an outlet 114 (e.g., a nozzle outlet), a tube 115 fluidly coupled to the nozzle 113, and an enema bulb 103 fluidly coupled to the tube 115. The term "fluidly coupled" may refer to the respective components as being physically connected to while permitting a liquid solution to pass in a one-directional or two-directional manner (e.g., depending on the presence, or lack thereof, of an anti-reflux diaphragm). The enema bulb 103 is configured to store solution (not shown) therein and, in response to a squeezing force applied to the enema bulb 103, direct the solution through the tube 115 and the nozzle 113, and expel the solution through the outlet 114.

The anti-reflux coupler 120 can be positioned between the enema bulb 103 and the tube 115 through which the solution passes from the enema bulb 103 to the tube 115. In some embodiments, the anti-reflux enemator 100 includes a first threaded connection 121 for detachably attaching the anti-reflux coupler 120 to the enema bulb 103, a second threaded connection 122 for detachably attaching the tube 115 to the anti-reflux coupler 120, and a third threaded connection 123 for detachably attaching the nozzle 113 to the tube 115. The first threaded connection 121 can include the first internal thread connector 105, which can mate with an external thread of the enema bulb 103, or a securing mechanism attached thereto.

Similarly, the second threaded connection 122 can include the second internal thread connector 109, which can mate with an external thread of the tube 115, or a securing mechanism attached thereto. The third threaded connection 123 can include the second external thread connector 111 and the third internal thread connector 112. While the tube 115 is shown coupled via the second internal thread connector 109, in other embodiments, the tube 115 or other device (e.g., a large nozzle) may be coupled to the second external thread connector 111. As such, the anti-reflux coupler 120 has different coupling mechanisms positioned on different portions of the body of the anti-reflux coupler 120.

In further embodiments, the anti-reflux enemator includes a first sealing ring 106 configured to prevent leakage occurring at the first threaded connection 121, a second sealing ring 108 configured to prevent leakage occurring at the second threaded connection 122, and a third sealing ring 110 configured to prevent leakage occurring at the third threaded connection 123.

Two one-way air valves can be positioned on the enema bulb 103 to facilitate a quick inflation of the enema bulb 103 after being squeezed by the operator. In some embodiments, the anti-reflux enemator 100 can include a first one-way air valve 101 and a second one-way air valve 102 positioned relative to an aperture 125 located at a base of the enema bulb 103.

Figure 7:
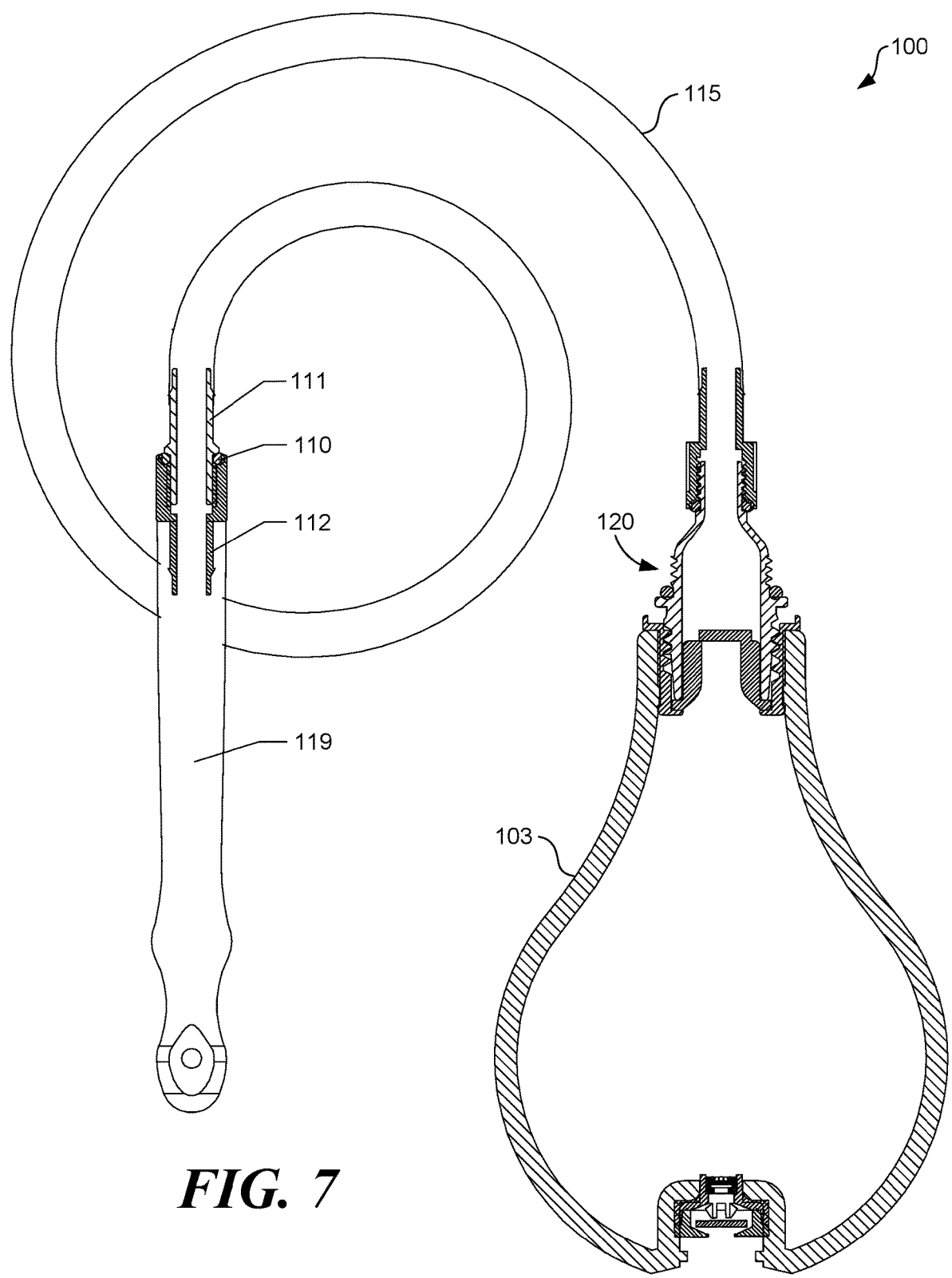
FIG. 7 is another cross-sectional view of an anti-reflux tube-type enemator according to various embodiments of the present disclosure.
Figure 8:
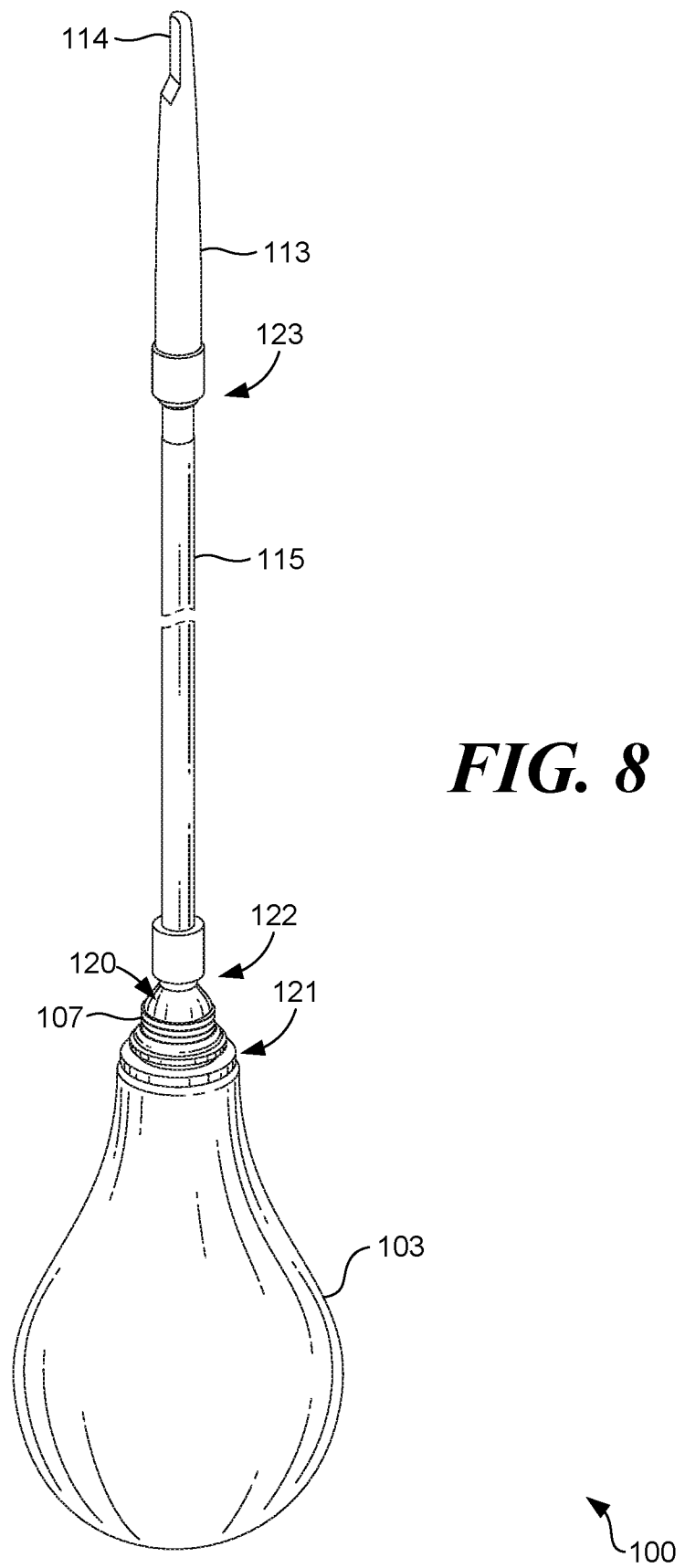
FIG. 8 is a perspective view of an anti-reflux tube-type enemator according to various embodiments of the present disclosure.
Figure 9:
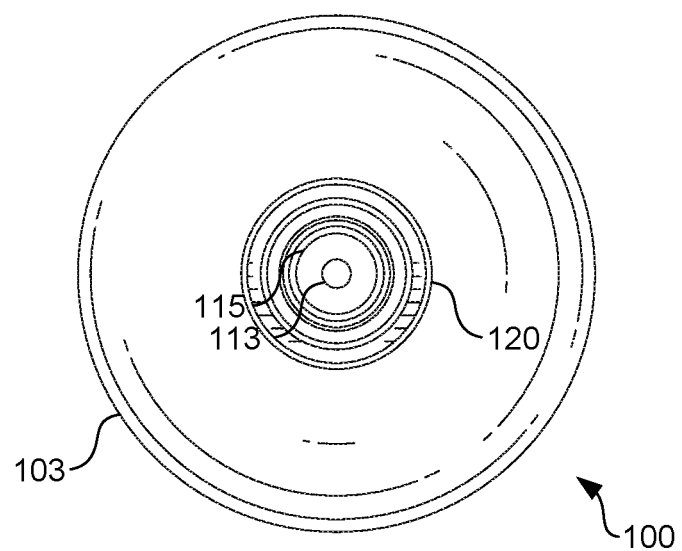
FIG. 9 is a top view of an anti-reflux tube-type enemator according to various embodiments of the present disclosure.
Figure 10:
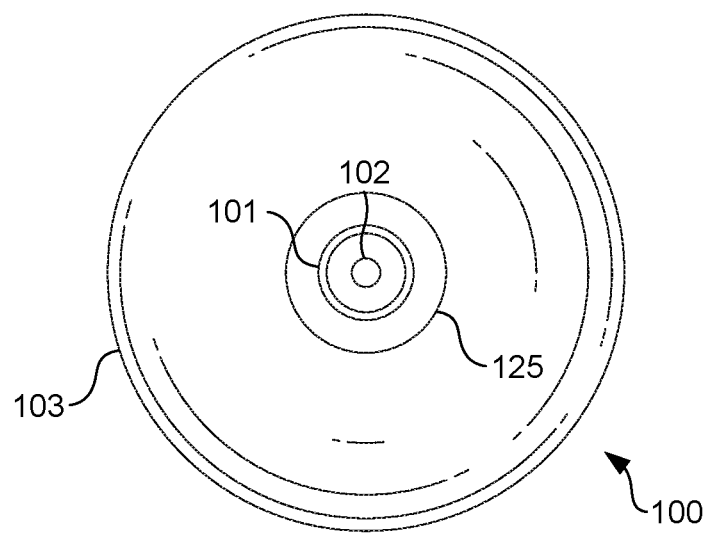
FIG. 10 is a bottom view of an anti-reflux tube-type enemator according to various embodiments of the present disclosure.

In some embodiments, the nozzle 113 of the anti-reflux enemator is a first nozzle having a first predetermined size and shape. The anti-reflux enemator 100 can further include a second nozzle 119 having a second predetermined size and shape different from the first predetermined size and shape, where the second nozzle 119 is configured to replace the first nozzle 113 via the third threaded connection 123. For instance, in some embodiments, the nozzle 113/119 can include a calabash-shaped syringe pipe body, as shown in FIG. 7. Alternatively, in some embodiments, the nozzle 113/119 can include straight syringe-type nozzle, as shown in FIG. 1.

Figure 6:
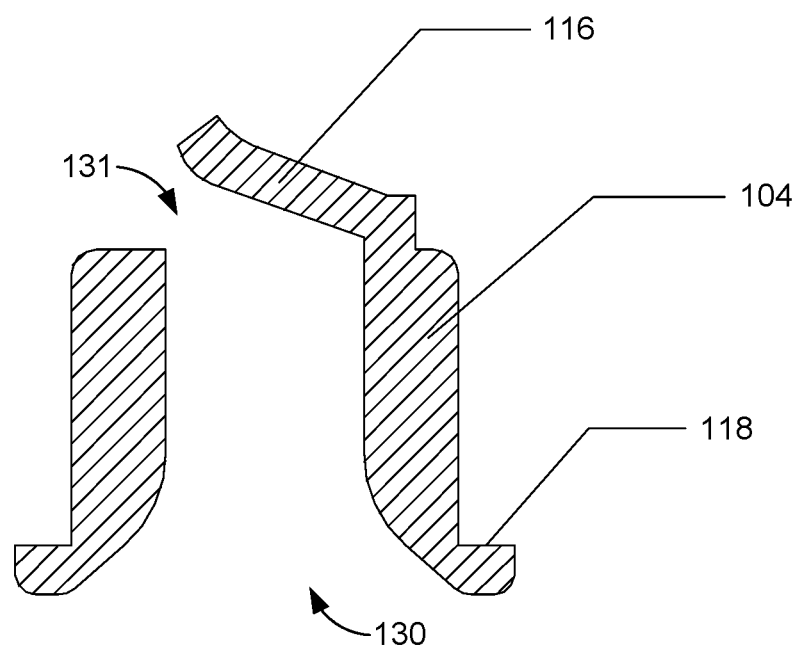
FIG. 6 is a schematic diagram of a water discharge state of a check valve of the anti-reflux tube-type enemator of FIG. 1 according to various embodiments of the present disclosure.

The anti-reflux coupler 120 can further include a check valve 104. As shown in FIG. 6, the check valve 104 can include an anti-reflux diaphragm 116. As such, in some embodiments, the check valve 104 can include one of an umbrella valve, a duckbill valve, a slit-cutting valve, and a flapper valve. In some embodiments, the check valve 104 is a silicone check valve comprising the sealing step surface 118. The sealing step surface 118 can be positioned at the lower part of the check valve 104, and the anti-reflux diaphragm 116 can be positioned at the top of the check valve 104, as can be appreciated.

Figure 3:
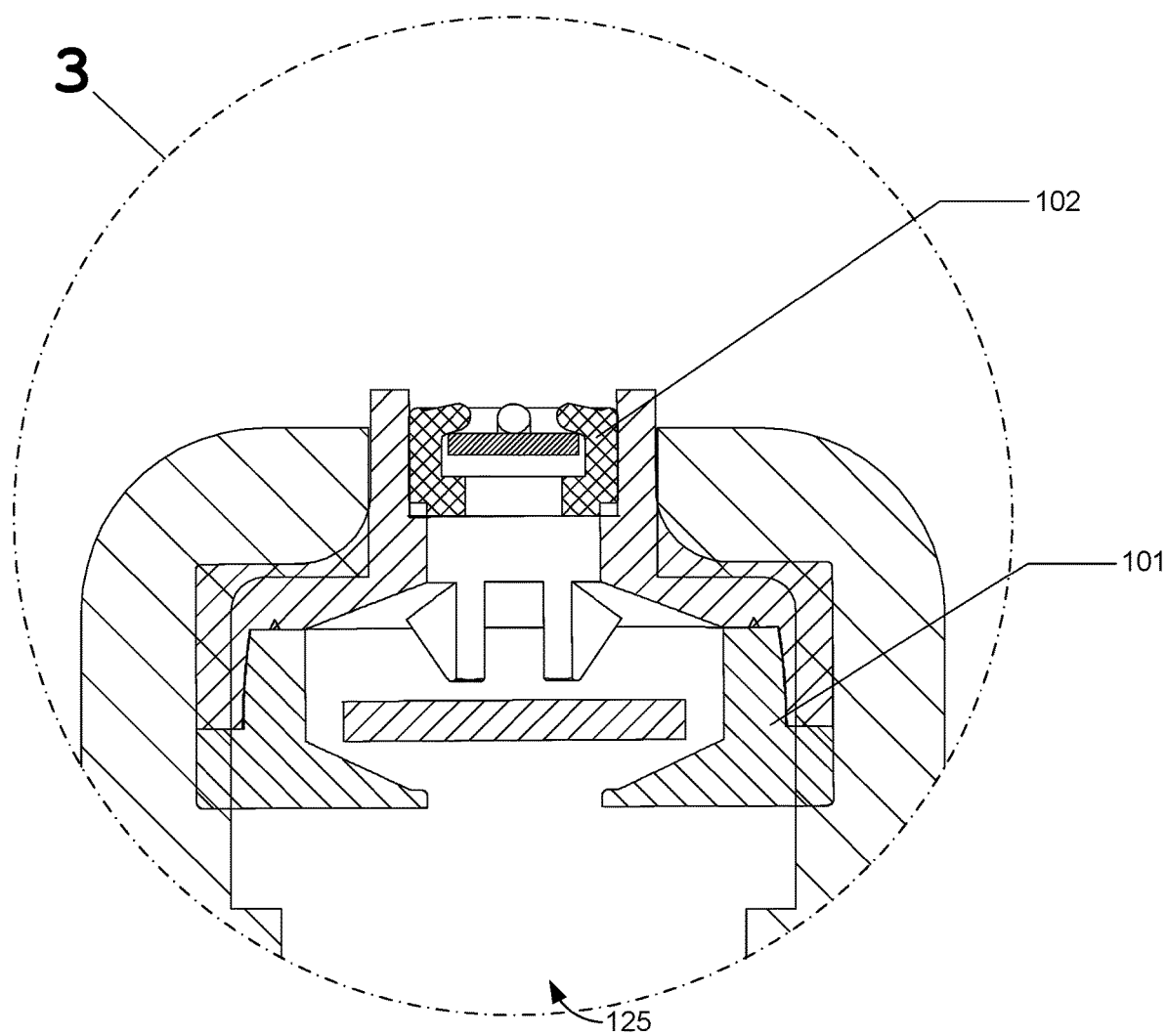
FIG. 3 is a partial enlarged view of callout region 3 of FIG. 1 according to various embodiments of the present disclosure.

Referring back to the cross-section view of the anti-reflux enemator 100 shown in FIGS. 1 and 3, the first one-way air valve 101 can be set at an intermediate position of a base or a bottom of the enema bulb 103. The second one-way air valve 102 can be inserted into the first one-way air valve 101 in some embodiments. Referring back to FIG. 1, the first internal thread connector 105 can be inserted into a top inlet of the enema bulb 103, and the first external thread connector 107 can be connected to the inner side thread of the first internal thread connector 105. The check valve 104 can be connected to the lower inner side thread of the first external thread connector 107.

The second internal thread connector 109 can be mounted on an upper outer thread of the first external thread connector 107. A first distal end of the tube 115 (e.g., a silicone tube) can be externally or internally mounted on the second internal thread connector 109. A second distal end of the tube 115 can be coupled with a second external thread connector 111. The other end of the second external thread connector 111 can be mounted with the third internal thread connector 112, and the bottom end of the third internal thread connector 112 can be mounted with a nozzle 113, such as a straight syringe-type nozzle shown in FIG. 1.

The first external thread connector 107 can be connected to the first sealing ring 106 at the middle thread. The first external thread connector 107 and the second internal thread connector 109 can be provided with a second sealing ring 108 at the junction, and the second internal thread connector 109 can be connected with the tube 115. The other end of the tube 115 can be connected to the second external thread connector 111. The second external thread connector 111 and the third internal thread connector 112 have the third sealing ring 110 positioned at their junction. An outlet 114 can be positioned on a side of the nozzle 113, and an inclined nozzle surface 117 (e.g., a bevel) can be further provided above the outlet 114.

In operation, when the solution filled in the enema bulb 103 is squeezed to supply solution, the solution is pushed against the anti-reflux diaphragm 116 of the check valve 104. The solution flows through the tube 115 to the nozzle 113, and flows out of the outlet 114 located at the top of the nozzle 113, for instance, to flow into the human body. At the same time, the solution is also subject to reflux by the counter-force of air pressure in the human body. At this time, the anti-reflux diaphragm 116 on the check valve 104 is covered by the counter-force to prevent the solution from flowing back into the enema bulb 103.

After the squeezing of the enema bulb 103 is stopped, the enema bulb 103 inhales air from outside of the first one-way air valve 101 and the second one-way air valve 102 positioned at the bottom by elastic rebound. After the enema bulb 103 rebounds to its original state, the first one-way air valve 101 and the second one-way air valve 102 at the bottom no longer intake air. At this time, the first one-way air valve 101 and the second one-way air valve 102 simultaneously prevent the solution from flowing out, which greatly reduces risk of solution leakage. In the process of supplying the solution, many sealing gaskets are used for sealing as described herein, and the check valve 104 is designed with a sealing step surface 118.

After the first external thread connector 107 is tightened, the sealing step surface 118 is pressed at the lower part of the check valve 104 and seals by itself, avoiding the anti-reflux enemator 100 from leaking water and preventing the solution inside the enema bulb 103 from flowing out.

Figure 4:
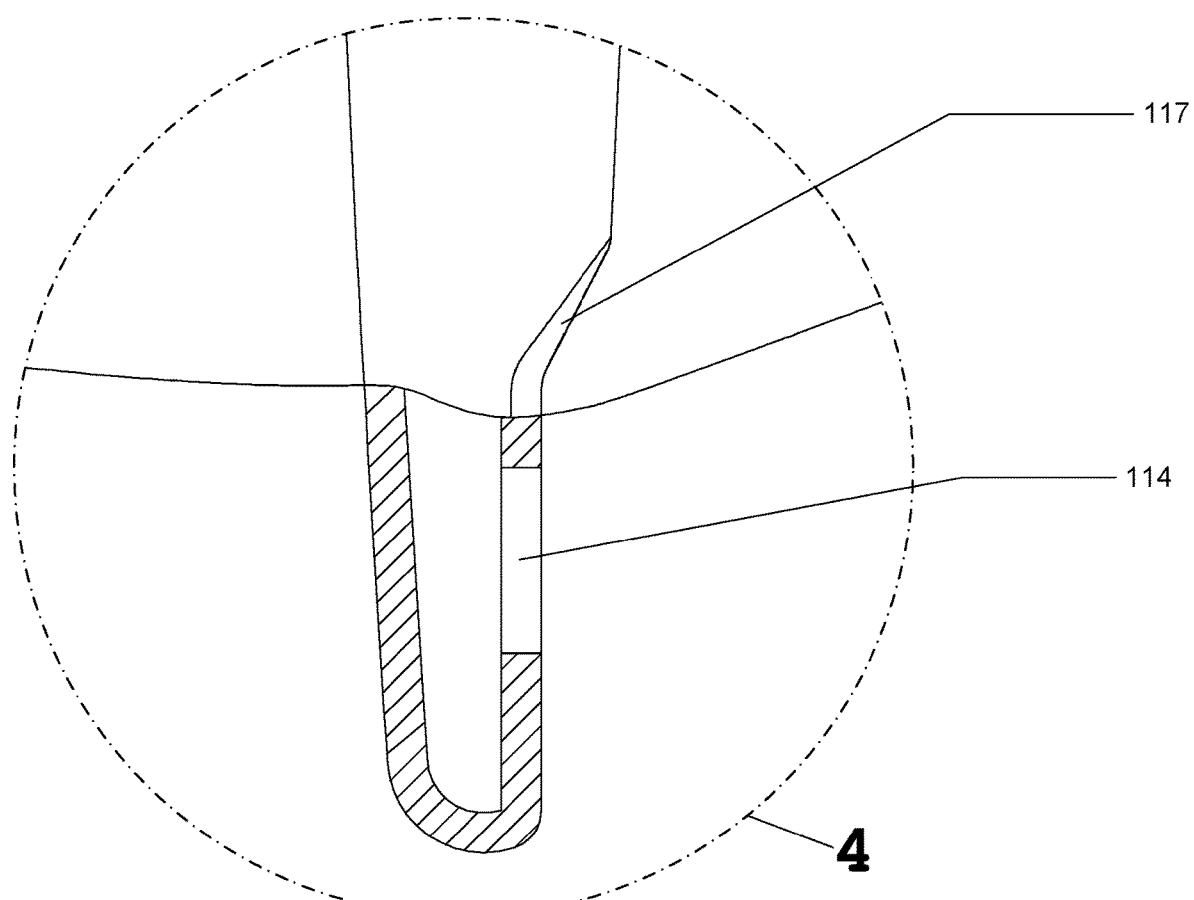
FIG. 4 is a partial enlarged view of callout region 4 of FIG. 1 according to various embodiments of the present disclosure.
Figure 5:
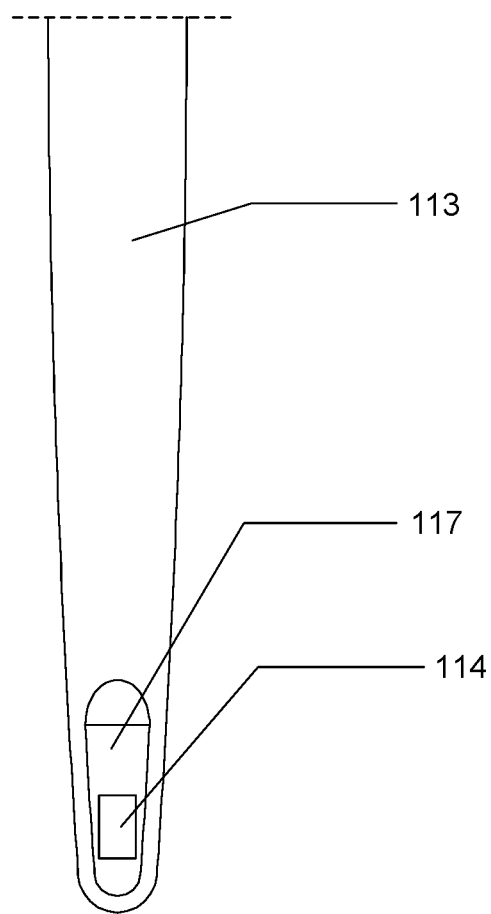
FIG. 5 is a front face view of a nozzle of the anti-reflux tube-type enemator of FIG. 1 according to various embodiments of the present disclosure.

Additionally, in embodiments in which the nozzle 113 includes a straight syringe nozzle, the nozzle 113 can employ a single-side flat design, and the outlet 114 can be positioned at the flat side, and the outlet 114 at the flat side is less likely to be blocked after entering the human body than the ordinary outer surface hole. Below the outlet 114, the inclined nozzle surface 117 (e.g., a bevel) is provided for a transitioning design to facilitate the solution flowing into the human body more smoothly, and the surface of the syringe nozzle has no joint line, no edges, and no sharp corners. The outlet 114 is set on a plane, where the injection mold is a plane mold, thereby avoiding generation of flash and burrs that can scratch the human body, as shown in FIGS. 4 and 5. The third internal thread connector 112 can be mounted inside the straight nozzle 113 for easy assembly and disassembly. The nozzle 113 can be connected to the tube 115, which is more convenient and flexible with a longer distance, and the connection is completely adopted of threads, providing more convenient disassembly and assembly and avoiding looseness.

Again, the anti-reflux coupler 120 can include an anti-reflux diaphragm 116 configured to prevent reflux of the solution into the enema bulb 103 from the tube 115 and/or nozzle 113. In some embodiments, the anti-reflux coupler 120 includes one or more inlets 130 for receiving at least a portion of the solution from an interior of the enema bulb 103 and an outlet 131 for expelling the solution into the tube 115 or nozzle 113.

The nozzles 113/119 can include dipping pipes, which are formed using a plastic dipping process, and the surface is smooth without a joint line. To this end, in some embodiments, the dipping process can include: (1) mold heating: heating in an oven at 200-250° (or 10 minutes, the first mold heating time needs to be appropriately lengthened, so as to avoid the mold temperature being too high, and the material thickness not being up to standard; the PVC material is heated to approximately 35~40° C.; (2) dipping: the mold is moved above the trough, the trough is raised to the required height for 3 to 8 minutes, and the dipping length between 120 and 140 mm is performed to avoid the product being scrapped when the cut product is not long enough, or the cut product is too long affecting the total length of the subsequent cut to increase the difficulty of operation; after the dipping is completed, the mold slowly leaves the dipping trough vertically, and is transferred into the oven for baking at the oven temperature of 160~190° C. for 580~620 seconds; (3) cooling and demolding: the device is removed from the oven area and placed in a cooling zone for 5 to 10 minutes. The time is determined according to the wall thickness of the product; the demolding operation is performed after proper cooling; (4) head trimming: Any bumps on the nozzle 113/119 are grinded into a circular arc shape by a polishing wheel, and then baked with a heat gun until the surface is smooth and shiny; (5) Cutting length: If the product is too long, cut the length of the product to 120-140 mm with a pipe cutter, and then use the cutter tool to cut off the excess part of the tail to make the total length reach 115-125 mm; (6) head punching: Three holes are punched in the three planes of the triangular head with tooling and 4~6 mm drill bit; (7) cleaning: Wipe the surface with a dust-free cloth to ensure that each of them is clean; (8) bonding plastic parts: The internal thread plastic parts are bonded to the inside; (9) inspection: inspect whether the appearance and hardness meet the requirements of the customer and whether the head is smooth; and (10) packaging: the nozzle 113/119 is placed neatly into the packaging carton to prevent deformation due to mutual extrusion.

The features, structures, or characteristics described above may be combined in one or more embodiments in any suitable manner, and the features discussed in the various embodiments are interchangeable, if possible. In the following description, numerous specific details are provided in order to fully understand the embodiments of the present disclosure. However, the person skilled in the art will appreciate that the technical solution of the present disclosure may be practiced without one or more of the specific details, or other methods, components, materials, and the like may be employed. In other instances, well-known structures, materials, or operations are not shown or described in detail to avoid obscuring aspects of the present disclosure.

Although the relative terms such as "on," "below," "upper," and "lower" are used in the specification to describe the relative relationship of one component to another component, these terms are used in this specification for convenience only, for example, as a a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

In this specification, the terms such as "a," "an," "the," and "said" are used to indicate the presence of one or more elements and components. The terms "comprise," "include," "have," "contain," and their variants are used to be open ended, and are meant to include additional elements, components, etc., in addition to the listed elements, components, etc. unless otherwise specified in the appended claims. The terms "first", "second", etc. are used only as labels, rather than a limitation for a number of the objects.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. An anti-reflux enemator, comprising:
   a nozzle comprising a nozzle outlet;
   a tube fluidly coupled to the nozzle;
   an enema bulb fluidly coupled to the tube, the enema bulb being configured to store solution therein and, responsive to a squeezing force applied to the enema bulb, direct the solution through the tube and the nozzle, and expel the solution through the nozzle outlet;
   an anti-reflux coupler positioned between the enema bulb and the tube through which the solution passes from the enema bulb to the tube, the anti-reflux coupler comprising:
      an inlet for receiving at least a portion of the solution from an interior of the enema bulb;
      an outlet for expelling the solution into the nozzle; and
      an anti-reverse diaphragm configured to prevent reflux of the solution into the enema bulb from the tube or the nozzle;
   a first threaded connection for detachably attaching the anti-reflux coupler to the enema bulb;
   a second threaded connection for detachably attaching the tube to the anti-reflux coupler;

a third threaded connection for detachably attaching the nozzle to the tube;
an aperture located at a base of the enema bulb;
a first one-way air valve nested in the aperture at an intermediate position of the base of the enema bulb;
a second one-way air valve inserted into the first one-way air valve;
a first sealing ring configured to prevent leakage occurring at the first threaded connection;
a second sealing ring configured to prevent leakage occurring at the second threaded connection; and
a third sealing ring configured to prevent leakage occurring at the third threaded connection.

2. The anti-reflux enemator of claim 1, wherein:
the nozzle of the enemator is a first nozzle having a first predetermined size and shape; and
the enemator further comprises a second nozzle having a second predetermined size and shape different from the first predetermined size and shape, the second nozzle being configured to replace the first nozzle via the third threaded connection.

3. The anti-reflux enemator of claim 1, wherein the anti-reflux coupler further comprises a check valve, the check valve comprising the anti-reverse diaphragm.

4. The anti-reflux enemator of claim 3, wherein the check valve comprises one of: an umbrella valve; a duckbill valve; a slit-cutting valve; and a flapper valve.

5. An anti-reflux enemator, comprising:
a nozzle comprising a nozzle outlet;
a tube fluidly coupled to the nozzle;
an enema bulb fluidly coupled to the tube, the enema bulb being configured to store solution therein and, responsive to a squeezing force applied to the enema bulb, direct the solution through the tube and the nozzle, and expel the solution through the nozzle outlet;
an anti-reflux coupler positioned between the enema bulb and the tube through which the solution passes from the enema bulb to the tube, the anti-reflux coupler comprising:
an inlet for receiving at least a portion of the solution from an interior of the enema bulb;
an outlet for expelling the solution into the nozzle; and
an anti-reverse diaphragm configured to prevent reflux of the solution into the enema bulb from the tube or the nozzle; and
an aperture positioned on the enema bulb;
a first one-way air valve nested in the aperture at an intermediate position of a base of the enema bulb; and
a second one-way air valve inserted into the first one-way air valve.

6. The anti-reflux enemator of claim 5, further comprising:
a first threaded connection for detachably attaching the anti-reflux coupler to the enema bulb;
a second threaded connection for detachably attaching the tube to the anti-reflux coupler; and
a third threaded connection for detachably attaching the nozzle to the tube.

7. The anti-reflux enemator of claim 6, further comprising:
a first sealing ring configured to prevent leakage occurring at the first threaded connection;
a second sealing ring configured to prevent leakage occurring at the second threaded connection; and
a third sealing ring configured to prevent leakage occurring at the third threaded connection.

8. The anti-reflux enemator of claim 5, wherein:
the nozzle of the anti-reflux enemator is a first nozzle having a first predetermined size and shape; and
the anti-reflux enemator further comprises a second nozzle having a second predetermined size and shape different from the first predetermined size and shape, the second nozzle being configured to replace the first nozzle via the third threaded connection.

9. The anti-reflux enemator of claim 5, wherein the anti-reflux coupler further comprises a check valve, the check valve comprising the anti-reverse diaphragm.

10. The anti-reflux enemator of claim 9, wherein the check valve comprises one of: an umbrella valve; a duckbill valve; a slit-cutting valve; and a flapper valve.

11. The anti-reflux enemator of claim 9, wherein the check valve is a silicone check valve comprising a step seal surface.

12. The anti-reflux enemator of claim 5, wherein the nozzle comprises an inclined nozzle surface such that a bottom portion of the nozzle has a width less than a top portion of the nozzle.

13. The anti-reflux enemator of claim 5, wherein the nozzle comprises a calabash-shaped syringe pipe body.

14. A method, comprising:
providing an anti-reflux enemator, the anti-reflux enemator comprising:
a nozzle comprising a nozzle outlet;
a tube fluidly coupled to the nozzle;
an enema bulb fluidly coupled to the tube, the enema bulb being configured to store solution therein and, responsive to a squeezing force applied to the enema bulb, direct the solution through the tube and the nozzle, and expel the solution through the nozzle outlet;
an anti-reflux coupler positioned between the enema bulb and the tube through which the solution passes from the enema bulb to the tube, the anti-reflux coupler comprising:
an inlet for receiving at least a portion of the solution from an interior of the enema bulb;
an outlet for expelling the solution into the nozzle; and
an anti-reverse diaphragm configured to prevent reflux of the solution into the enema bulb from the tube or the nozzle; and
an aperture positioned on the enema bulb;
a first one-way air valve nested in the aperture at an intermediate position of a base of the enema bulb; and
a second one-way air valve inserted into the first one-way air valve.

15. The method of claim 14, wherein the anti-reflux enemator as provided further comprises:
a first threaded connection for detachably attaching the anti-reflux coupler to the enema bulb;
a second threaded connection for detachably attaching the tube to the anti-reflux coupler;
a third threaded connection for detachably attaching the nozzle to the tube;
a first sealing ring configured to prevent leakage occurring at the first threaded connection;
a second sealing ring configured to prevent leakage occurring at the second threaded connection; and
a third sealing ring configured to prevent leakage occurring at the third threaded connection.

16. The method of claim 14, wherein:
the nozzle of the anti-reflux enemator is a first nozzle having a first predetermined size and shape;
the method further comprises providing a second nozzle having a second predetermined size and shape different from the first predetermined size and shape; and
replacing the first nozzle with the second nozzle via the third threaded connection.

17. The method of claim 14, wherein:
the anti-reflux coupler further comprises a silicon check valve, the silicon check valve comprising the anti-reverse diaphragm and a step seal surface; and
the silicon check valve comprises one of: an umbrella valve; a duckbill valve; a slit-cutting valve; and a flapper valve.

18. The method of claim 14, wherein the nozzle comprises an inclined nozzle surface such that a bottom portion of the nozzle has a width less than a top portion of the nozzle.

19. The method of claim 14, wherein the nozzle comprises a calabash-shaped syringe pipe body.

\* \* \* \* \*